United States Patent [19]

Bohl

[11] 4,298,574

[45] Nov. 3, 1981

[54] HYDROGEN GAS DETECTOR

[75] Inventor: Thomas L. Bohl, Madison, Ohio

[73] Assignee: The Babcock & Wilcox Company, New Orleans, La.

[21] Appl. No.: 111,046

[22] Filed: Jan. 10, 1980

Related U.S. Application Data

[60] Continuation of Ser. No. 940,049, Sep. 6, 1978, abandoned, which is a division of Ser. No. 51,664, Jun. 25, 1979, Pat. No. 4,222,900.

[51] Int. Cl.³ .............................................. G01N 27/16
[52] U.S. Cl. .................................... 422/97; 73/27 R; 422/98
[58] Field of Search .................................. 422/94–98; 23/232 E; 338/34; 73/27 R

[56] References Cited

U.S. PATENT DOCUMENTS

| | | | |
|---|---|---|---|
| 2,349,250 | 5/1944 | Doan | 23/232 E |
| 2,904,406 | 9/1959 | Moore | 422/95 X |
| 3,437,446 | 4/1969 | Pierce | 252/472 X |
| 3,479,257 | 11/1969 | Shaver | 422/95 X |
| 3,549,327 | 12/1970 | Fergusson | 422/94 X |
| 3,866,460 | 2/1975 | Pearce, Jr. | 422/95 X |
| 4,063,898 | 12/1977 | Fisher | 422/94 |

FOREIGN PATENT DOCUMENTS 461039  11/1949  Canada ............................ 252/472

Primary Examiner—Arnold Turk
Attorney, Agent, or Firm—Vytas R. Matas; Joseph M. Maguire

[57] ABSTRACT

A differential thermocouple hydrogen gas detector (10) is provided by coating one thermocouple junction (34) of a differential thermocouple pair (34, 36) with a Palladium-Silver alloy catalyst (46) and the other thermocouple junction (36) with a non-catalyst (52). Heated hydrogen gas reacts with the catalyst (46) to liberate heat to the catalyst coated thermocouple junction (34) in proportion to the concentration of hydrogen gas and proportionally raise the temperature of the catalyst coated junction (34) above that of the non-catalyst coated junction (36). The output signal (44) from the differential thermocouple device (34, 36) thus provides an output signal indicative of the concentration of hydrogen gas.

6 Claims, 4 Drawing Figures

HYDROGEN GAS DETECTOR

This is a continuation of application Ser. No. 940,049, filed Sept. 6, 1978, now abandoned, from which a divisional application Ser. No. 051,664, was filed on June 25, 1979, and which issued as U.S. Pat. No. 4,222,900.

TECHNICAL FIELD

The present invention relates to gas detectors generally and particularly to differential thermocouple devices modified to detect and monitor hydrogen gas content.

BACKGROUND ART

Several methods have been and are being used to analyze gas streams for hydrogen. Among those still in use are gas chromatography, thermal conductivity, differential pressure across a Palladium membrane, catalytic combustion and surface absorption sensors.

Gas chromatography can be very accurate, sensitive, and a selective method of analyzing gas for hydrogen content but is a batch process and real-time continuous data cannot be obtained. Also the hardware associated with such a measuring technique is relatively expensive.

Thermal conductivity techniques for analyzing gas for hydrogen content provide continuous data, but these devices and techniques are not selective and cannot discriminate between gases having similar thermal conductivities, and are affected by all gases in the sample stream. Thus it must be known beforehand that certain gases are not present before such measuring techniques may be utilized.

Catalytic combustion sensors are used to analyze gas for hydrogen content. They are relatively inexpensive, have fast response time, and good sensitivity. Their problem is however also a lack of selectivity as they will detect all combustibles gases, usually with different gain factors, making data from streams with mixed combustibles practically useless.

Differential pressure across a Palladium membrane is a known method of testing for hydrogen content. It is extremely selective for hydrogen, but present forms of the known devices lack sensitivity and have time constants in the order of 3 minutes. Therefore, even though these are continuous measurement instruments, the long time constant nearly precludes them as real-time hydrogen gas analyzers in process applications.

Differential thermocouples are known for use in thermal analysis as evidenced by U.S. Pat. Nos. 3,906,721 and 4,063,898. However the Applicant is unaware of any such prior art devices wherein such known differential thermocouples are respectively coated with an activated Palladium or activated Palladium-Silver alloy catalyst and a non-catalyst to provide a self-powered, highly responsive, inexpensive, and stable hydrogen gas detector ideally suited for process applications.

SUMMARY OF THE INVENTION

In accordance with the present invention a differential thermocouple hydrogen gas detector is provided which is quick responding, inexpensive, compact, self-powered and stable. One thermocouple junction of the differential thermocouple pair is coated with an activated Palladium or activated Palladium-Silver alloy catalytic material to allow heated hydrogen gas to chemically react with the catalyst to liberate heat and to raise the temperature of the catalyst coated thermocouple junction above ambient in proportion to the concentration of the hydrogen gas. The other thermocouple junction of the differential thermocouple pair is coated with a noncatalytic material such as a high temperature glass such as Pyrex or a high temperature epoxy to prevent any reaction at that junction. This non-catalytic coating allows the second junction to only monitor ambient temperature. The differential connection of the thermocouple pair in opposition allows the ambient temperature signals sensed by both thermocouple junctions to cancel leaving only the signal from the temperature increase over ambient being sensed by the differential thermocouple pair. The differential thermocouple thus establishes an output signal proportional to the concentration of hydrogen gas which is independent of the ambient temperature.

In one specific embodiment of the invention the catalyst coated junction is formed by crimping an activated Palladium-Silver alloy tube around the catalytic thermocouple junction.

In certain situations the hydrogen gas may have to be heated to a threshold temperature at which it will react with the activated Palladium-Silver alloy catalyst. A coal heater may be mounted around the two thermocouple junctions to heat the hydrogen gas. An alternate method is to heat the gas by passing it through a heated block prior to exposing it to the differential thermocouple pair.

In view of the foregoing it will be seen that one aspect of the present invention is to provide a differential thermocouple hydrogen gas detector.

Another aspect of the present invention is to provide an activated Palladium-Silver alloy hydrogen gas detector which is highly responsive to hydrogen and which is insensitive to other gases.

These and other aspects of the present invention will be more fully understood upon consideration of the following description of the preferred embodiment in conjunction with the associated drawings.

DESCRIPTION OF THE PREFERRED EMBODIMENT

Figure 1:
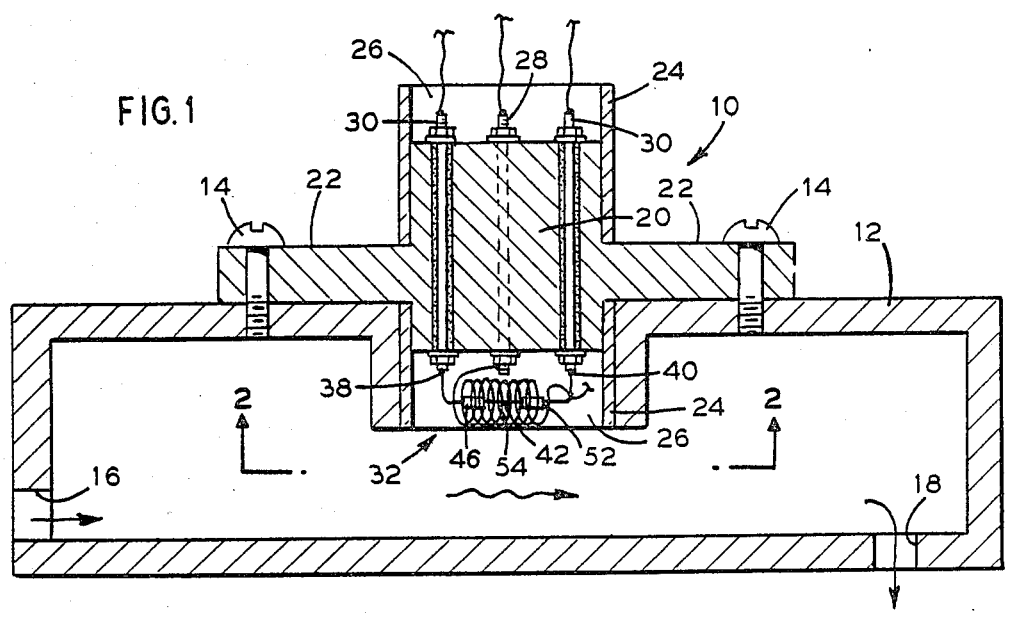
FIG. 1 is a side view of the hydrogen gas detector of the present invention.
Figure 2:
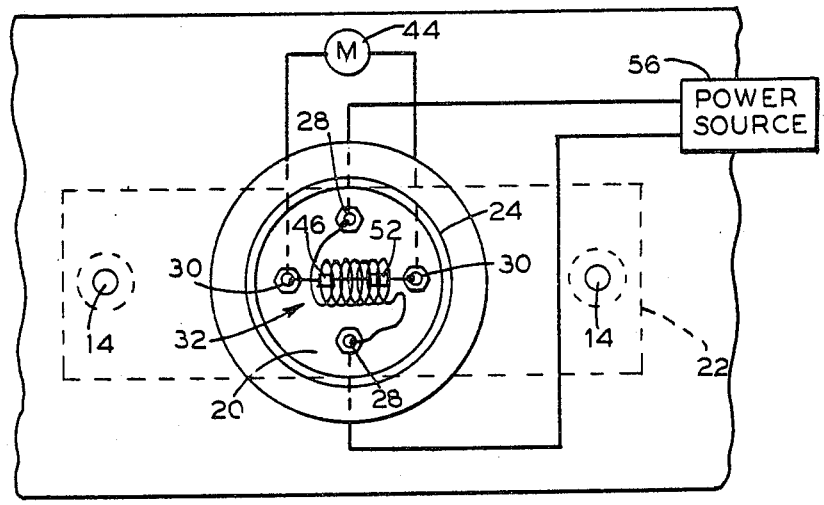
FIG. 2 is a bottom plan view of the detector taken along lines 2—2 of FIG. 1.

Referring now to the drawings, FIGS. 1 and 2 disclose a hydrogen gas detector assembly 10 mounted to a block 12 by screws 14. The block 12 is designed to allow gases which include hydrogen gas to flow through the block 12 from the inlet 16 to an outlet 18 so as to come in contact with the hydrogen detector assembly 10. The block 12 may be a part of a complete gas sampling analyzing system also including an oxygen detector as is described in U.S. Pat. No. 3,960,500 issued June 1, 1976 which provides for recirculation of flue gases from a duct and back thereto. Further details of such a gas sampling analyzing system are available in the mentioned patent and the reader is referred thereto for any further required clarification.

The hydrogen detector assembly 10 includes a metal block 20 having mounting flanges 22 through which screws 14 sealably mount the hydrogen detector assembly 10 to the block 12. This wall tubing 24 is pressed onto the block 20 on both ends of the flanges 22 to extend beyond the ends of the metal block 20 and to provide a protected space 26 at both ends of the metal block 20. Two pairs of electrical leads 28 and 30 are extended through the block 20 to be electrically isolated therefrom and to have ends extending into the spaces 26. The electrical leads 28 and 30 may be brass with gold flash; however, nickel has also been found to be a suitable material.

The heart of the detector assembly 10 is a specially coated differential thermocouple assembly 32 which is electrically connected across the electrical leads 30.

Figure 3:
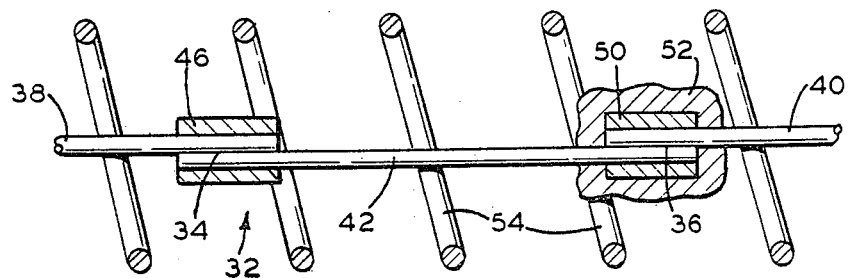
FIG. 3 is an expanded cut-away side view of the thermocouple junctions of the FIG. 1 detector.

As may be best seen in FIG. 3, the differential thermocouple assembly 32 has a first thermocouple junction 34, and a second thermocouple junction 36 each produced by overlapping the ends of Alumel wires 38 and 40 with a common connecting wire 42 of Chromel. As is known, the formed thermocouple junctions 34 and 36 will induce opposing millivoltage electrical potentials depending on the temperatures of the respective junctions 34 and 36. These millivoltage potentials will be sensed along the electrical leads 30 by virtue of the connection of the thermocouple assembly 32 thereby to a voltmeter 44 connected to the opposite ends of the electrical leads 30. To have the thermocouple assembly 32 act as a hydrogen gas detector, the respective thermocouple junctions 34 and 36 must be respectively coated with catalytic and non-catalytic material. To accomplish this, as well as to allow for ease of manufacture, the catalytic thermocouple junction 34 is formed by threading the ends of the Alumel wire 38 and one end of the Chromel wire 42 into an activated Palladium-Silver alloy tube 46 and crimping the tube 46 onto the ends of the mentioned wires. The composition of the tube 46 is 75% Palladium and 25% Silver by weight. The tubing 46 is a piece of 1/16 inch O.D.×0.003 inch wall 75% Palladium-25% Silver alloy tubing which was activated to be hydrogen responsive by first etching it in concentrated nitric acid for one minute, water rinsing, and then further etching it in boiling Potassium-hydroxide for one minute. The etching in nitric acid is used to dissolve part of the silver matrix from the inner and more importantly the outer surface of the Palladium-Silver alloy tubing 46 which will be the sensing surface of the catalyst coated thermocouple assembly 32. This etching provides an increased hydrogen reactive outer surface area of the tubing 46. The further treatment of the tube 46 in boiling Potassium-hydroxide etches the Palladium on the important outer surface of tube 46 and forms numerous catalytically active sites in the crystalline structure of the alloy. These sites are believed to be a Potassium-Oxygen-Palladium complex making the treated outer surface catalytic to hydrogen.

Clearly, pure Palladium could also be used. However it would also have to be similarly activated by etching to form the mentioned Potassium-Oxygen-Palladium complex on the surface the surface to make the surface catalytic to hydrogen.

The non-catalytic thermocouple junction 36 is formed by threading the ends of the Alumel wire 40 and the common Chromel wire 42 into a brass tube 50 and crimping the tube 50 onto the thermocouple junction 36 to retain it thereto. To further insure the noncatalytic aspects of the thermocouple junction 36, the brass tube 50 is coated with a high temperature glass 52 such as Pyrex.

The ability of the described catalytic and noncatalytic coated thermocouple junctions to operate as a hydrogen gas detector rests on the fact that activated Palladium and certain of its alloys will absorb only hydrogen and its isotopes providing a natural selectivity for hydrogen. When the sensor is heated to about 400° F., catalytic combustion takes place on the catalytic surface, but only preferentially for hydrogen. The activated Palladium-Silver alloy catalyst does not react with carbon monoxide or methane under these conditions. The chemical equation for this described phenomenon may be given as follows:

$$H_2 + \tfrac{1}{2} O_2 \xrightarrow[\text{catalyst}]{\text{Palladium}} H_2O + \text{heat}$$

To insure that the gases flowing through the catalyst and non-catalyst coated thermocouple junctions are above the required threshold temperature of 400° F. a spiral heater 54 is wrapped around the catalytic coated thermocouple junction 34 and the non-catalytic coated thermocouple junction 36. The heater 54 is connected across the electrical leads 28 with the opposite ends of the electrical leads 28 being connected to a suitable power source 56 which provides energy to the heater 54.

From the foregoing it will be now readily seen that the thermocouple assembly 32 is ideally suited to monitor hydrogen gas in the gases entering the inlet 16 and exiting through the outlet 18. In combustion processes using natural gas a knowledge of the degree of combustion occurring is vital. Different amounts of gas such as hydrogen will be indicative of the degree of complete combustion and thus the output of the thermocouple assembly 32 may be used to control the combustion process. The hydrogen will react with the activated Palladium-Silver alloy on the catalytic coated thermocouple junction 34 to produce and liberate heat to the catalytic coated thermocouple junction 34. The more hydrogen present in the flue gases, the more will be produced and the more heat will be liberated to the catalytic coated thermocouple junction 34. The non-catalytic coated thermocouple junction 36 will not provide any kind of a reaction liberating heat to the junction 36 and as such will only measure the ambient temperature common to both the non-catalytic coated thermocouple junction 36 and the catalytic coated thermocouple junction 34. Because of the electrical connection of the two coated thermocouple junctions 34 and 36 and their sharing of a common ambient temperature, the ambient temperature effect will be cancelled out, leaving only the temperature rise above ambient produced at the catalytic coated thermocouple junction 34 as a result of the chemical reaction occurring at the activated Palladium-Silver alloy surface 48.

Figure 4:
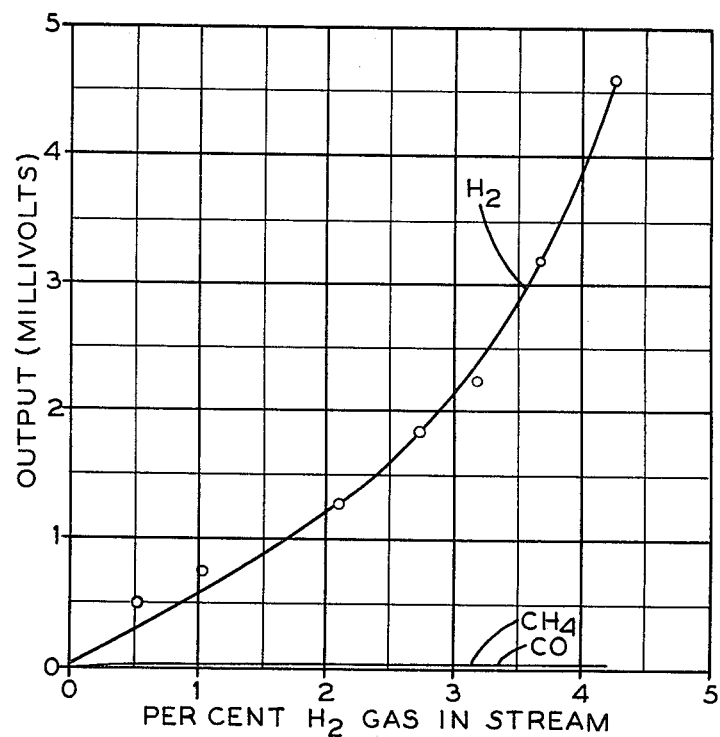
FIG. 4 is a data curve of the output of the FIG. 1 detector vs different levels of hydrogen in a gas stream.

Clearly the greater the hydrogen content the more heat will be released to the catalytic coated junction and the greater the millivoltage signal produced by the differential thermocouple assembly 32. Referring to FIG. 4 it may be seen that when the differential thermocouple assembly 32 was exposed to a gas stream of a 600 cc/min flow rate having a hydrogen gas content varied from 0%–4.25% the millivolt output signal from the assembly 32 varied from 0–4.5 millivolts. Clearly this type of signal is very adaptable to the providing of adequate control signals for process control.

To insure that no other catalytic reaction occurs at various elements of the detector assembly 10 which would influence the measure of combustible gases by the detector assembly 10, special care must be taken in the choice of metals used for forming the thermocouple junctions or the heater. As a precaution, the Applicant has found it desirable to coat the heater 54 with an inert material such as high temperature glass. Similarly, there is a possibility that the Chromel-Alumel thermocouple wires may be attacked by sulfuric acid fumes. As a precaution from such attack as well as to prevent any possible catalytic reaction on the wires, such wires could also be coated with glass.

Certain modifications and improvements will occur to those skilled in the art upon reading this specification. It will be understood that all such improvements and modifications have been deleted herein for the sake of conciseness and readability but are properly within the scope of the following claims.

I claim:

1. A detector for monitoring hydrogen gas in a stream comprising:
   a first thermocouple junction located in the gas stream;
   a second thermocouple junction located in the gas stream and connected to said first thermocouple to form a differential thermocouple;
   catalytic means having numerous catalytic sites formed around said first thermocouple junction from etching said catalytic means with Potassium-hydroxide allowing hydrogen in the gas stream to selectively react with said catalytic means above a predetermined threshold temperature to liberate heat and increase the temperature of said first thermocouple above ambient temperature;
   heater means for maintaining said first thermocouple junction above the predetermined threshold temperature;
   insulation means formed around said second thermocouple junction to prevent hydrogen in the gas stream from reacting with said second thermocouple junction to liberate heat thereby making said second thermocouple junction measure only ambient temperature; and
   indicating means connected to said first and second thermocouple junctions to measure the temperature difference measured by said first and second thermocouple junctions to provide an indication of hydrogen content in the gas stream.

2. A detector as set forth in claim 1 wherein said heater means includes a coil heater mounted around said first and second thermocouple junctions.

3. A detector as set forth in claim 1 wherein said catalytic means includes an activated Palladium-Silver alloy tube mounted on said first thermocouple junction which is activated by etching with Potassium-hydroxide to form the catalytic sites on the tube making it sensitive to hydrogen.

4. A detector as set forth in claim 3 wherein said activated Palladium-Silver alloy is 75% Palladium and 25% Silver by weight.

5. A detector as set forth in claim 4 wherein said insulating means includes a tube of noncatalytic material mounted on said second thermocouple.

6. A detector as set forth in claim 5 wherein said tube is formed from brass material and wherein said insulating means further includes a high temperature glass material formed around said brass tube.

* * * * *